United States Patent
Cellier et al.

(10) Patent No.: US 10,077,464 B2
(45) Date of Patent: Sep. 18, 2018

(54) MICRO-ORGANISM DETECTION MEDIUM COMPRISING AT LEAST ONE ALKYL(THIO)GLYCOSIDE

(71) Applicant: Biomérieux, Marcy-l'Etoile (FR)

(72) Inventors: Marie Cellier, Montalieu-Vercieu (FR); Sylvain Orenga, Neuville-sur-Ain (FR); John Perry, Tyne and Wear (GB)

(73) Assignee: Biomerieux, March-l'etoile (FR)

( * ) Notice: Subject to any disclaimer, the term of this patent is extended or adjusted under 35 U.S.C. 154(b) by 0 days.

(21) Appl. No.: 14/655,224

(22) PCT Filed: Dec. 24, 2013

(86) PCT No.: PCT/FR2013/053259
§ 371 (c)(1),
(2) Date: Jun. 24, 2015

(87) PCT Pub. No.: WO2014/102503
PCT Pub. Date: Jul. 3, 2014

(65) Prior Publication Data
US 2015/0329897 A1 Nov. 19, 2015

(30) Foreign Application Priority Data

Dec. 28, 2012 (FR) ...................... 12 62965

(51) Int. Cl.
*C12Q 1/44* (2006.01)
*C12Q 1/04* (2006.01)
*C12Q 1/10* (2006.01)

(52) U.S. Cl.
CPC .............. *C12Q 1/44* (2013.01); *C12Q 1/045* (2013.01); *C12Q 1/10* (2013.01); *G01N 2333/255* (2013.01)

(58) Field of Classification Search
None
See application file for complete search history.

(56) References Cited

U.S. PATENT DOCUMENTS

| | | | |
|---|---|---|---|
| 4,892,817 | A | 9/1990 | Pawlak |
| 5,210,022 | A | 5/1993 | Roth |
| 8,216,802 | B2 | 7/2012 | Casse et al. |
| 8,334,112 | B2 | 12/2012 | Monget et al. |
| 8,420,345 | B2 | 4/2013 | Orenga et al. |
| 8,497,086 | B2 | 7/2013 | Roche et al. |
| 2005/0014215 | A1* | 1/2005 | Gilbert ............. C12N 1/20 435/34 |
| 2005/0148044 | A1* | 7/2005 | Rambach .......... C12Q 1/045 435/34 |
| 2008/0145879 | A1 | 6/2008 | Orenga et al. |
| 2010/0062467 | A1* | 3/2010 | Monget et al. |
| 2015/0329897 | A1 | 11/2015 | Cellier et al. |

FOREIGN PATENT DOCUMENTS

| | | |
|---|---|---|
| EP | 1790734 A1 | 5/2007 |
| EP | 2107119 A | 10/2009 |
| FR | 2697028 A1 | 4/1994 |
| WO | WO 2002/040706 A2 | 5/2002 |
| WO | WO 2010/128120 A2 | 11/2010 |
| WO | WO2011/107703 * | 9/2011 |
| WO | WO 2012/161992 A1 | 11/2012 |
| WO | WO 2014/043616 A1 | 3/2014 |
| WO | WO 2014/102503 A1 | 7/2014 |
| WO | 2014/161864 A1 | 10/2014 |

OTHER PUBLICATIONS

"WO 2011107703 A1" English machine translation, 2011, 48 pages of PDF.*
International Search Report for PCT/FR2013/053259 dated Apr. 15, 2014.
Baumstummler et al. "Development of a Nondestructive Fluorescence-Based Enzymatic Staining of Microcolonies for Enumerating Bacterial Contamination in Filterable Products" 2010, *J. Applied Microbiol.* 110:69-79.
Agban et al., "Synthesis of Indigogenic Substrates. Investigation of *Salmonella* Esterase Activity," *Eur. J. Med. Chem.* (1990), 25:697-699.
Dickinson et al., "Stability of Emulsions Containing Both Sodium Caseinate and Tween 20,"*J. Colloid Interface Sci.* (1999), 212:466-473.
International Search Report for PCT/EP2014/056544 dated Jun. 27, 2014.
Looney et al., "Evaluation of the ATB 32 A System for Identification of Anaerobic Bacteria Isolated from Clinical Specimens," J. Clin. Microbiol. (Jul. 1990), 28(7):1519-1524.
Orenga et al., "Enzymatic Substrates in Microbiology," J. Microbiol. Meth. (2009), 79:139-155.
Rice et al., "Assay for β-Glucuranidase in Species of the Genus *Escherichia* and Its Applications for Drinking-Water Analysis," Applied Environ. Microbiol. (Feb. 1991), 57(2):592-593.
Von Graevenitz et al., "RADIPEC UR, a 2-h Miniaturized System for Pinpointing Uropathogens," J. Clin. Microbiol. (Jan. 1998), 26(1):151-152.
Satta et al., "Phosphatase Activity Is a Constant Feature of All Isolates of All Major Species of the Family Enterobacteriaceae," J. Clin. Microbiol. (Jan. 1, 1988), 26(12):2637-2641.
Barber, et al., "Identification of *Staphylococcus pyogenes* by the Phosphatase Reaction", Journal of Pathology and Bacteriology, vol. 63, No. 1, Jan. 1, 1951, pp. 65-68.
Bobey et al., "Rapid Detection of Yeast Enzymes by Using 4-Methylumbelliferyl Substrates", Journal of Clinical Microbiology, vol. 13, No. 2, Feb. 1, 1981, pp. 393-394.
First Examination Report for EP14714282.2 dated Oct. 17, 2017.

* cited by examiner

Primary Examiner — Kade Ariani
(74) Attorney, Agent, or Firm — Husch Blackwell LLP

(57) ABSTRACT

A microorganism detection medium, said detection being based on showing the presence of a microbial enzyme activity chosen from esterase and/or osidase and/or peptidase and/or sulfatase and/or phosphatase activities of microorganisms, preferably said microbial enzyme activity being an esterase activity, said medium comprising:
at least one chromogenic and/or fluorogenic substrate specific to the enzyme activity sought, preferably specific to an esterase activity,
at least one alkyl(thio)glycoside,
at least one solvent (S).

14 Claims, No Drawings

MICRO-ORGANISM DETECTION MEDIUM COMPRISING AT LEAST ONE ALKYL(THIO)GLYCOSIDE

CLAIM OF PRIORITY

The present application is a National Stage filing under 35 U.S.C. § 371 of International Patent Application No. PCT/FR2013/053259, filed on Dec. 24, 2013 and entitled "MICROORGANISM DETECTION MEDIUM COMPRISING AT LEAST ONE ALKYL(THIO)GLYCOSIDE," which claims the benefit of and priority to French Patent Application No. 1262965, filed on Dec. 28, 2012, both of which are incorporated by reference herein in their entireties.

TECHNICAL FIELD

The present invention relates to microbiological analysis by biochemical means, and more particularly by enzymatic means. More specifically, the present invention relates to the detection of microorganisms (for example bacteria strains) by seeding reaction media, in particular for the purposes of characterisation (identification of said microorganisms, determination of the potential properties of resistance of the latter to at least one antimicrobial agent, etc.) and/or of enumeration of said microorganisms. These reaction media comprise chromogenic and/or fluorogenic substrates capable of reacting with the microbial enzymes specific to the microorganisms sought.

PRIOR ART

Within the framework of the present invention, of most particular interest is the detection of pathogenic microorganisms or quality indicators (in particular for the purpose of characterising and/or enumerating them), whether in the medical environment or the industrial environment, and more particularly of microorganisms with enzyme activity of the esterase (comprising in particular the carboxylesterase, lipase and phospholipase activities), osidase, peptidase, sulfatase or phosphatase type, for example the bacteria or yeasts of the genera *Salmonella, Escherichia, Pseudomonas, Listeria, Staphylococcus, Enterococcus, Candida*, and, more specifically, the detection of bacteria of the genus *Salmonella* based on showing the presence of/detecting an esterase enzyme activity.

The strains of *Escherichia coli* are often revealed by showing the presence of an osidase-type enzyme activity such as β-glucuronidase or β-galactosidase activity.

In the same manner, the genus *Listeria* is detected by showing the presence of β-glucosidase activity.

An aminopeptidase activity may also be used to reveal a group, a genus or a species of microorganisms. L-alanine-aminopeptidase activity, for example, makes it possible to differentiate Gram-negative bacteria from Gram-positive bacteria.

The genus *Salmonella*, which is responsible for various severe infections in humans (typhoid fever, food poisoning), possesses non-specific esterases capable of hydrolysing synthetic chromogenic, for example indigogenic, substrates.

Salmonellae—and more generally esterase-activity bacteria—are conventionally detected and characterised in culture broth or on agar media, which enable the detection and the characterisation of suspected colonies of esterase-activity bacteria, in particular salmonellae. The seeding of such media takes place by contacting the biological sample with the medium.

Bacteria with esterase, osidase, peptidase, sulfatase or even phosphatase activities possess in their enzyme assets esterases, osidases, peptidases, sulfatases or phosphatases which cleave the target bonds of the synthetic enzyme substrates present in the medium, and thus free the activated chromophore or fluorophore part of said substrates. This results in a coloration or a fluorescence which reveals the hydrolysis, and therefore the presence of target bacteria or colonies of target bacteria.

To be able to perform large-scale routine tests, it is necessary that the detection and/or characterisation and/or enumeration media be stable and make it possible to simplify to the greatest possible extent the corresponding detection and/or characterisation and/or enumeration methods, by limiting the instances of manipulation. Furthermore, it is important that the methods offer very good sensitivity (intensity of coloration or of fluorescence), as well as a first-rate specificity of detection (in order to limit or even avoid the detection of "false positives"). The rate of revelation of the suspected colonies is also a fundamental parameter of these types of media and methods for detecting bacteria which exhibit the above-mentioned enzyme activities.

It is known that the synthetic substrates of enzymes such as the esterases, osidases, peptidases, sulfatases or phosphatases pose compatibility problems with the culture media for microorganisms and in particular for bacteria possessing these activities. Moreover such substrates are not stable over time, which leads to a reduction in sensitivity to the enzyme activity concerned as the storage time increases.

In this context, the scientific article entitled "*Synthèse de substrata indigogèniques. Mise en èvidence de l'activité estérasique des salmonelles*" [Synthesis of indigogenic substrates. Showing the presence of the esterase activity of salmonellae]: A. Agban et al., *Eur. J. Med. Chem.* (1990) 25, 697-699, made known agar culture media comprising indigogenic substrates, namely in particular bromo-5-indoxyl pelargonate (C9) and a bile salt, namely sodium deoxycholate. Such culture media suffer from the same disadvantages as those set out below with reference to document FR-A-2697028.

Patent application FR-A-2697028 discloses a culture medium for showing the presence of salmonellae comprising a chromogenic esterase substrate constituted by an ester of caprylic acid with an indole residue (5-bromo-4-chloro-3-indolyl-caprylate), as well as a detergent chosen from the bile salts (sodium deoxycholate). This chromogen and this bile salt are contained in a nutrient medium which permits the growth of the salmonellae. According to the teaching of patent application FR-A-2697028, the bile salt is added directly to the selective medium in which the esterase substrate is already included. However, this culture medium does not offer all the desirable guarantees in terms of stability of the esterase substrate. Furthermore, it turns out that this latter is not completely miscible with the culture medium. This evidently impairs the quality of the results obtained with regard to sensitivity (intensity of the coloration obtained), rapidity and stability. It should also be noted that the culture medium according to FR-A-2697028 takes the form of powder. This obliges the user to perform a prior operation to reconstitute the liquid or gelled medium. This restriction results from the lack of stability of the esterase substrates employed.

Another disadvantage linked to the use of bile salts—such as sodium deoxycholate—is based on the fact that the latter are raw materials of animal origin, from which a degree of variability in terms of quality originates.

Furthermore, the results obtained with the culture medium according to FR-A-2697028 are perfectible in terms of biological activity.

The patent EP-B-1334206, in the name of the Applicant, describes a medium for detecting/identifying microorganisms (and in particular bacteria and/or yeasts) with enzyme activity chosen from esterase and/or osidase and/or peptidase and/or sulfatase and/or phosphatase activities. This medium, in liquid or agar form, ready-to-use and storage-stable, comprises in particular:

at least one substrate of esterases, osidases and/or peptidases and/or sulfatases and/or phosphatases, which is chromogenic or fluorogenic, and at least one sorbitan fatty acid ester (SFAE), or at least one fatty acid (FA) or an SFAE/FA mixture, as an emulsifying stabilising agent (in a certain percentage by weight), and optionally at least one solvent (S).

Still according to EP-B-1334206, SFAE is selected, preferably, from the group comprising:

polyoxyethylene sorbitan monolaurate comprising 20 units of ethylene oxide (E.O.),-TWEEN® 20-;

polyoxyethylene sorbitan monopalmitate (20 E.O.),-TWEEN® 40-;

polyoxyethylene sorbitan monostearate (20 E.O.),-TWEEN® 60-;

polyoxyethylene sorbitan tristearate (20 E.O.),-TWEEN® 65-;

polyoxyethylene sorbitan monooleate (20 E.O.),-TWEEN® 80-;

polyoxyethylene sorbitan sesquioleate (20 E.O.),-TWEEN® 83-;

polyoxyethylene sorbitan trioleate (20 E.O.),-TWEEN® 85-;

and mixtures thereof.

Sorbitan fatty acid esters (SFAE) are known surface active agents widely used in food and pharmaceutical preparations. By way of illustration, we can cite the article by DICKINSON et al.: "*J Colloid interface Sci* 1999 Apr. 15; 212 (2): 466-473" concerning the stabilisation of emulsions containing sodium caseinate and a polyoxyethylene sorbitan monolaurate comprising 20 units of ethylene oxide (TWEEN® 20). The emulsions considered are oil-in-water emulsions (30% volume of n-tetradecane at pH 6.8).

Although the detection sensitivity of the reaction medium according to EP-B-1334206 is relatively satisfactory, there is a need to develop a microorganism detection medium based on showing the presence of a microbial enzyme activity chosen from esterase and/or osidase and/or peptidase and/or sulfatase and/or phosphatase activities of microorganisms, and offering superior performances to those obtained by employing the prior art media, and in particular that of patent EP-B-1334206. Superior performances can be taken to mean a heightened detection sensitivity, namely the highest possible coloration and/or fluorescence intensities for the colonies of the target microorganisms. This turns out to be particularly desirable with regard to the detection of the salmonellae by showing the presence of an esterase activity. Furthermore, and in addition to the requisite sensitivity criterion, it is also important that the abovementioned microorganism detection medium is reliable, specific and reproducible.

One objective of the present invention is to develop a microorganism detection medium (in particular for the purposes of characterising and/or enumerating them) based on showing the presence of a microbial enzyme activity chosen from esterase and/or osidase and/or peptidase and/or sulfatase and/or phosphatase activities of microorganisms, which includes at least one enzyme substrate chosen from esterase substrates and/or osidase substrates and/or peptidase substrates and/or sulfatase substrates and/or phosphatase substrates, which is chromogenic and/or fluorogenic and which is storage-stable (intensity of the revelation coloration or fluorescence of maintained at a maximum level for at least several weeks).

Another objective of the invention is to obtain a microorganism detection medium based on showing the presence of a microbial enzyme activity selected from esterase and/or osidase and/or peptidase and/or sulfatase and/or phosphatase activities of microorganisms, which does not take the form of a dry powder to be regenerated with a liquid to reconstitute a liquid or gelled medium, but which comes directly in ready-to-use forms.

Another objective of the invention aims to reduce the quantities of chromogenic and/or fluorogenic enzyme substrate(s) used, which the person skilled in the art knows to be particularly expensive.

Yet another objective of the invention consists in developing a method of obtaining the abovementioned detection medium which is simple to employ, and which in particular makes it possible to characterise the microorganisms sought (in particular via their identification and/or the determination of their potential resistance properties to at least one antimicrobial agent), and/or to enumerate them without excessive difficulty.

Other objectives will become apparent upon reading the present application.

Statement of the Invention

The present invention aims to meet the aforementioned need, and to achieve all or some of the objectives mentioned above.

As a consequence, a first object of the invention relates to a microorganism detection medium, said detection being based on showing the presence of a microbial enzyme activity chosen from esterase and/or osidase and/or peptidase and/or sulfatase and/or phosphatase activities of microorganisms, preferably said microbial enzyme activity being an esterase activity, said medium comprising:

at least one chromogenic and/or fluorogenic substrate specific to the enzyme activity sought, preferably specific to an esterase activity, at least one alkyl(thio)glycoside, at least one solvent (S).

According to a preferred embodiment, when the microorganism detection medium according to the invention comprises n-octyl-β-D-glucopyranoside as the alkylglycoside, said medium does not comprise compound(s) comprised in the group constituted by sodium polyphosphates (HMP), rubidium chloride (RbCl) and lithium chloride (LiCl).

Another object of the invention relates to a microorganism detection medium, said detection being based on showing the presence of a microbial enzyme activity chosen from esterase and/or osidase and/or peptidase and/or sulfatase and/or phosphatase activities of microorganisms, preferably said microbial enzyme activity being an esterase activity, said medium mainly consisting of:

at least one chromogenic and/or fluorogenic substrate specific to the enzyme activity sought, preferably specific to an esterase activity, at least one alkyl(thio)glycoside, at least one solvent (S), and optionally a culture medium suitable for allowing the growth of the microorganisms sought (target microorganisms).

Another object of the invention is also a microorganism detection medium, said detection being based on showing the presence of a microbial enzyme activity chosen from esterase and/or osidase and/or peptidase and/or sulfatase and/or phosphatase activities of microorganisms, preferably said microbial enzyme activity being an esterase activity, said medium consisting of:

at least one chromogenic and/or fluorogenic substrate specific to the enzyme activity sought, preferably specific to an esterase activity, at least one alkyl(thio)glycoside, at least one solvent (S), a culture medium suitable for allowing the growth of the microorganisms sought (target microorganisms).

In practice, the person skilled in the art shall choose the culture medium depending upon the target microorganisms (and in particular depending upon the target bacteria), according to criteria which are perfectly known to and within the reach of this person skilled in the art. This culture medium does not comprise compound(s) comprised in the group constituted by sodium polyphosphates (HMP), rubidium chloride (RbCl) and lithium chloride (LiCl).

The term alkyl(thio)glycoside must be understood, in terms of the present invention, as being able to designate an alkylglycoside-type compound (namely in which the alkyl part is bound to the carbohydrate residue via an ether bond —O—), or an alkylthioglycoside-type compound (namely in which the alkyl part is bound to the carbohydrate residue via a thioether bond —S—), which is why the root "thio" appears in brackets in this term.

Said alkyl part is generally aliphatic, linear or branched, saturated or unsaturated. "Aliphatic" alkyl part can be understood to mean, in the sense of the present invention, a linear or open branched (acyclic) part. According to a preferred embodiment, the alkyl part of the alkyl(thio)glycoside compound is a linear (non-branched), advantageously saturated, aliphatic radical.

The carbohydrate residue, for its part, may be a simple sugar (monosaccharide) or oside (saccharide) residue. The terminology alkyl(thio)glycoside therefore covers, in terms of the present invention, both alkyl(thio)glycosides and alkyl(thio)polyglycosides, able to be used alone or optionally in association with other surface active agents, such as one or more anionic surface active agents.

These alkyl(thio)glycosides are non-ionic surface active agents conventionally used in a large range of industrial applications, and in particular in detergents or cosmetics.

Without being bound by the following theory, the alkyl (thio)glycoside(s) used for the purpose of the present invention appears/appear to act as stabilising-emulsifying agent(s). They may be associated, according to one particular embodiment, with at least one synergic co-agent, preferably, at least one anionic surface active agent, preferably 7-ethyl-2-methyl-4-undecyl hydrogen sulfate or at least one of its salts, and more particularly its sodium salts (TERGITOL-4®).

The different methods of obtaining alkyl(thio)glycosides according to the present invention are well known to the person skilled in the art. He/she shall therefore be able to, as desired, procure them on the market or synthesise them by employing his/her general knowledge or based on the existing publications on this subject.

Advantageously, at least one alkylglycoside is used as an alkyl(thio)glycoside.

The "detection medium" according to the invention must be understood as being able to consist of:

a medium which makes it possible to detect/disclose the presence or absence of microorganisms, in particular microorganisms sought (target microorganisms), and/or a medium which makes it possible to characterise said microorganisms, namely in particular to identify and/or determine their potential resistance properties to at least one anti-microbial agent (antibiotic agent in the case of bacteria), and/or a medium which makes it possible to enumerate said microorganisms; this enumeration consists in counting the number of colonies of microorganisms having grown on the reaction medium according to the invention, by employing microbiology techniques well known to the person skilled in the art.

The invention therefore also relates to a microorganism characterisation (for example identification) and/or enumeration medium, said characterisation and/or said enumeration being based on showing the presence of a microbial enzyme activity chosen from esterase and/or osidase and/or peptidase and/or sulfatase and/or phosphatase activities of microorganisms, preferably said microbial enzyme activity being an esterase activity, said medium comprising:

at least one chromogenic and/or fluorogenic substrate specific to the enzyme activity sought, preferably specific to an esterase activity, at least one alkyl(thio)glycoside, preferably at least one alkylglycoside, and at least one solvent (S).

According to a preferred embodiment, the enzyme activity of which the presence is shown (which is sought) is an esterase activity of the carboxylic ester hydrolase type, such as a carboxylesterase, lipase or phospholipase activity.

The microorganisms detected by using the culture medium according to the invention are, preferably, bacteria and/or yeasts, advantageously bacteria.

According to a particularly preferred embodiment, the reaction medium according to the invention is used to detect microorganisms (such as bacteria and/or yeasts) with esterase activity and, preferably, bacteria with esterase activity such as salmonellae (for example for the purposes of characterising and/or enumerating them). As is known to the person skilled in the art, esterase enzyme activity is very widespread in the field of microbiology. Indeed, numerous bacteria are known to possess an esterase activity and therefore are capable of cleaving the synthetic (chromogenic and/or fluorogenic) substrates specific to such enzyme activity. In addition to the salmonellae mentioned previously, it is also possible to cite the bacteria belonging to the genera *Pseudomonas, Acinetobacter, Listeria*, etc.

The detection of the aforementioned microorganisms consists in disclosing (visualising) their presence in/on a culture medium, via visual or optical detection of coloration(s) and/or fluorescence(s) which have appeared in the liquid medium, or on the colonies formed by these microorganisms on an agar medium. In the case of optical detection, this latter may be carried out by optical reading of all or part of said medium with the aid of devices such as a camera. The detection of coloration(s) and/or fluorescence(s) by optical reading enables a partial or total automation of the corresponding detection method.

Fluorogenic enzyme substrates may be of different natures. Firstly, substrates based on umbelliferone or aminocoumarin and its derivatives substituted in position 3, 4 or 6, make it possible to release a fluorescent compound varying from blue to green in colour under an ultraviolet (UV) lamp (λex=365 nm).

There are also substrates based on resorufin (and derivatives thereof) resulting in the release of a fluorescent compound pink under natural light (λex=530 nm).

It is also possible to cite substrates based on fluorescein (and derivatives thereof) which, after degradation, release a fluorescent compound yellow under natural light (λex=485 nm).

These fluorogenic enzyme substrates are generally not very suitable for use in agar media, and are preferably used in a liquid medium.

The chromogenic enzyme substrates usable in terms of the present invention may be of different natures.

Firstly, mention should be made of substrates based on indoxyl and derivatives thereof which, in the presence of oxygen, produce a precipitate varying from blue to pink, as well as derivatives of ALDOL™ (BIOSYNTH AG)—which are mentioned in the international application WO 2010/128120—which produce a coloured precipitate varying from yellow to red, including in the absence of oxygen. These substrates based on indoxyl and derivatives thereof are particularly preferred in terms of the present invention due to their relatively easy employment and their good detection sensitivity. Their applications mainly relate to the enzyme activities of the osidase, esterase and phosphatase type. Well suited to use on a solid or semi-solid support (filter, agar, electrophoresis gel, etc.), they are less so for use in a liquid medium (forming a precipitate).

Secondly, there are enzyme substrates based on hydroxyquinoline, dihydroxyflavone, dihydroxyanthraquinone, catechol or esculetin and derivatives thereof which, in the presence of iron salts, produce a coloured precipitate. There too, their applications mainly relate to enzyme activities of the osidase and esterase type.

Thirdly, mention can be made of enzyme substrates based on nitrophenol and nitroaniline and derivatives thereof, which result in the formation of a yellow compound. They make it possible to detect osidase and esterase activities in the case of nitrophenol-based substrates and peptidase activities in the case of nitroaniline-based substrates. However, in the case of the detection of peptidase activities, the released nitroaniline is toxic for the bacteria desired to be identified or characterised, which can prove to be detrimental to ongoing or subsequent analyses. Moreover, they are generally not suitable for use on a solid support, and better suited to use in a liquid medium.

Fourthly, there are enzyme substrates based on naphthol and naphthylamine and derivatives thereof. In this case, the enzyme-substrate reaction takes place in two steps, naphthol or naphthylamine released by enzyme activity undergoes "azo-coupling" in the presence of a diazonium salt which is added upon revelation, leading to the formation of an insoluble coloured compound. They make it possible to detect osidase and esterase activities by means of naphthol, and peptidase activities by means of naphthylamine. The "azo-coupling" reaction takes place in a medium which is often chemically aggressive, toxic to bacteria and which makes the sample unusable for other analyses, in addition naphthylamines are carcinogenic.

In terms of the present invention, the microorganisms which have grown on or in the detection medium according to the invention are detected and/or enumerated—visually or via an optical and electronic device of the camera or photographic apparatus type—via the appearance of coloured and/or fluorescent reactions (according to whether a chromogenic or fluorescent substrate is used) or displaying both characteristics simultaneously, said coloured and/or fluorescent reactions being produced by the targeted microbial enzyme activity.

More specifically concerning the enzyme substrates of esterases, the latter comprise, according to a preferred embodiment, 2 to 16 carbon atoms, with the length of the chain defining the intended application. Thus, the use of C2 or C4 substrates is suitable for detecting a maximum of "universal substrate" germs. For more specific applications, such as in particular detection of Salmonellae, C7-C10 substrates are particularly suitable. Among the chromogens capable of being bound to a C2-C12 carbon chain, it is possible to cite, for example, indoxyl-based substrates such as 5-bromo-4-chloro-3-indoxyl, 5-bromo-6-chloro-3-indoxyl, 6-chloro-3-indoxyl, 5-bromo-3-indoxyl, 5-iodo-3-indoxyl, 6-bromo-3-indoxyl and 5,6-dibromo-3-indoxyl, dihydroxyanthraquinone-based substrates such as alizarin; ALDOL™-based substrates (developed by Biosynth AG, Rietlisstrasse 4,9422 Staad, Switzerland, mentioned in particular within international patent application 2010/128120); the fluorophores being for example, 4-methylumbelliferone, and other derivatives of 7-hydroxycoumarin.

Such esterase enzyme substrates may be, for example, indoxyl-derived chromogenic ester substrates, and in particular 5-bromo-4-chloro-3-indoxyl caprylate, 5-bromo-6-chloro-3-indoxyl caprylate, 5-bromo-3-indoxyl nonanoate, 6-chloro-3-indoxyl nonanoate or 5-bromo-3-indoxyl decanoate. In this regard, mention should also be made of anthraquinone-derived chromogenic esterase substrates such as 2-alizarin octanoate.

In any event, these chromogenic and/or fluorogenic synthetic substrates are well known to the person skilled in the art, who will know to select the enzyme substrate(s) to be used depending upon the enzyme activity or activities sought.

According to a preferred embodiment of the present invention, the alkyl(thio)glycoside corresponds to the general formula (I):

$$R\text{---}X\text{-}(G)_n \qquad (I)$$

wherein:
R represents a linear or branched, saturated or unsaturated, aliphatic radical, preferably linear, advantageously linear and saturated, containing 2 to 12 carbon atoms, preferably 6 to 12 carbon atoms, and preferably 8 to 12 carbon atoms,
X is —O— or —S—, preferably —O—,
G represents a carbohydrate residue,
n is an integer between 1 and 10, preferably between 1 and 3, advantageously n is the integer 1 or 2.

Such a definition of the alkyl(thio)glycoside(s) according to the invention makes it possible to obtain the desired level of detection sensitivity, namely makes it possible to obtain very good coloration and/or fluorescence intensities from the chromogenic and/or fluorogenic enzyme substrates used. Without being bound by the theory, it is probable that this/these alkyl(thio)glycoside(s)—in particular those of general formula (I)—improve the detection of the targeted enzyme expressions, namely the microbial esterase and/or osidase and/or peptidase and/or sulfatase and/or phosphatase activities.

The detection medium according to the present invention may comprise one alkyl(thio)glycoside or a plurality of alkyl(thio)glycosides (namely at least two alkyl(thio)glycosides), which preferably correspond to the general formula (I) mentioned above. When the detection medium comprises at least two alkyl(thio)glycosides, the latter may be identical or different, all preferably corresponding to said general formula (I).

The preferred alkyl(thio)glycosides, in terms of the present invention, are the following alkylglycosides: n-octyl-β-D-glucopyranoside and n-dodecyl-β-D-maltoside (the latter being particularly preferred).

The microorganism detection medium according to the present invention is capable of being obtained by mixing at least one chromogenic and/or fluorogenic substrate specific to the enzyme activity sought (preferably specific to an esterase activity) and at least one alkyl(thio)glycoside such as defined previously in the solvent (S).

Quite significantly and in particular with regard to the problems mentioned in the preamble of the present application, the microorganism detection medium according to the invention is in a ready-to-use form (liquid or agar) and storage-stable, which means that the coloration and/or fluorescence intensity is kept stable at least for several weeks, advantageously for at least three weeks.

Preferably, the concentration of the alkyl(thio)glycoside(s) in the medium is between 0.5 g/L and 8 g/L, preferably between 0.5 g/L and 6 g/L, depending on the alkyl(thio)glycoside or alkyl(thio)glycosides used.

The solvent (S) is an aid for solubilising the chromogenic and/or fluorogenic enzyme substrate of interest, in particular with regard to a chromogenic enzyme substrate. It also supplements the action of the alkyl(thio)glycoside(s) which act(s) as stabilising-emulsifying agent(s).

According to an advantageous embodiment of the present invention, the solvent (S) is selected from the group comprising:
  alcohols, preferably methanol, ethanol, methoxyethanol,
  polar aprotic solvents, preferably dimethylformamide (DMF), dimethylsulfoxide (DMSO),
  aqueous solvents, preferably water or buffered water,
  and mixtures thereof;
preferably said solvent (S) is dimethylsulfoxide (DMSO).

In practice, the solvents preferably used are methanol or a polar aprotic solvent, preferably DMF and DMSO (preferably DMSO). In particular, when esterase substrates are used, the latter are dissolved in an organic solvent of the DMSO type, to which the alkyl(thio)glycoside(s) of interest is/are added.

With regard to the chromogenic and/or fluorogenic substrate, the latter comprises a target part specific to the enzyme whose presence is to be shown, preferably a target part specific to an esterase activity, and a chromophore and/or fluorophore marker part, said marker part emitting a light and/or a fluorescence when it is no longer associated with said target part, namely after cleavage by said enzyme.

According to a preferred embodiment, the enzyme substrate is a chromogenic or fluorogenic substrate, constituted by a target part of the enzyme to be detected and by a chromophore or fluorophore part, the target being selected, preferably, from the group comprising in particular:
  glycosides, constituted by mono-, di- and/or polysaccharide units, α- or β-bound to the hydroxyl function of the fluorophore or chromophore part;
  α-amino acids or peptides;
  organic acids, such as —O—CO(CH$_2$)$_n$—CH$_3$, where n is between 0 and 20;
  inorganic acids, such as sulfate, phosphate, pyrosulfate or phosphodiester;
  Quinones/Anthraquinones and derivatives, in particular Dihydroxyanthraquinone (Alizarin);
  aminocoumarins or hydroxycoumarins and derivatives;
  fluoresceins and derivatives;
  indoxyls or ALDOL™ and derivatives;
  aminophenols and derivatives;
  nitrophenols and derivatives;
  aminophenyls or hydroxyphenyls and derivatives;
  phenoxazinones and derivatives;
  catechols and derivatives;
  quinazolinones and derivatives (including ELF®97);
  dihydroxyflavone and derivatives;
  3-hydroxyflavone (3-HF) and derivatives;
  esculetin and derivatives.

Preferably, the enzyme substrate is a substrate based on indoxyl or on one of its derivatives. In this case, the invention also relates to a detection medium suitable for use in anaerobic and/or microaerophilic conditions (molecular oxygen concentration in the reaction medium lower than the atmospheric concentration), said medium comprising an agent which promotes the oxidative polymerisation of the indoxyl derivative, such as an ammonium ferric citrate complex.

Potassium permanganate, Ferricyanate/Ferricyanide can also be cited as "agents which promote oxidative polymerisation of the indoxyl derivative".

The agent which promotes oxidative polymerisation of the indoxyl derivative (for example a metal complex of the ammonium ferric citrate type) is used, preferably at a concentration of between approximately 0.1 and approximately 2 mg/ml (preferably around 0.6 mg/ml).

The concentration at which the enzyme substrate must be used in the reaction medium according to the invention can be easily determined by the person skilled in the art on the basis of his/her general knowledge and, where applicable, from routine tests. This concentration must be sufficient to achieve the required level of detection sensitivity but not be too great, in order to not risk inhibiting the growth of the microorganisms.

By way of example, the concentration of chromogenic and/or fluorogenic substrate is between 1 mg/L and 10 g/L, preferably between 5 mg/L and 6 g/L, advantageously between 25 mg/L and 2 g/L.

Advantageously, the reaction medium according to the invention comprises a suitable culture medium such as a medium described in the "Handbook of culture media" (CRC Press), preferably said culture medium being selected from:
  MacConkey, Hektoen selective media, selective chromogenic media intended for selectively detecting *salmonella* of the chromID® *Salmonella*, Columbia ANC, PALCAM, Sabouraud gentamycin-chloramphenicol type, preferably the MacConkey medium or a selective chromogenic medium intended for selectively detecting *salmonella* of the chromID® *Salmonella* type,
  non-selective media of the Columbia+/−blood, Trypticase Soy Agar (TSA), nutrient agar, Sabouraud type, preferably the Columbia medium In practice, the person skilled in the art shall choose the culture medium depending upon the target microorganisms (and in particular depending upon the target bacteria), according to criteria which are perfectly known to and within the reach of this person skilled in the art.

Without that being in any way limiting, it emerges that the medium according to the invention is particularly suitable for the detection (in particular for characterisation and/or enumeration purposes) of microorganisms of medical or industrial interest, and in particular among Gram-negative bacteria, more particularly those of the genus *Salmonella* and *Pseudomonas*.

As indicated throughout the present application, one of the main objectives is to develop a medium which makes it possible to detect the microorganisms (and in particular bacteria) which possess an esterase activity (in particular for characterisation and/or enumeration purposes), such as the bacteria of the genera *Salmonella, Pseudomonas, Acinetobacter*, etc.

With respect to detection of salmonellae, the MacConkey medium, the Hektoen medium or the chromID® *Salmonella* medium, for example, shall be chosen as the culture medium.

Furthermore, the medium may potentially contain other additives such as, for example: one or more other enzyme substrate(s), which are, for example, chromogenic and/or fluorogenic, peptones, one or more growth factor(s), carbohydrates, one or more selective agent(s), buffers, one or more gelling agent(s), etc.

The reaction medium according to the present invention takes a ready-to-use form, preferably a liquid or gel form. Ready-to-use form can be understood to mean a form ready to be seeded in a tube, flask or on Petri dishes.

One of the advantages of the reaction medium according to the invention is that it is capable of being stored for several weeks at 4° C. in liquid or gel form.

Another object of the invention relates to a method of obtaining a medium according to the invention, said method comprising the following steps:
a) preparing at least one stock solution of at least one chromogenic and/or fluorogenic substrate such as defined above and of at least one alkyl(thio)glycoside in the solvent (S),
b) optionally adding at least one additive into said medium, and
c) homogenising the whole.

With regard to the aforementioned step a) it should be noted that said substrate and said at least one alkyl(thio) glycoside may be added during the same step into the solvent (S) or, according to a alternative, said substrate is introduced into the solvent (S) in a first stage and then said at least one alkyl(thio)glycoside is taken up with the solution previously obtained (comprising said substrate solubilised by said solvent (S)).

Advantageously, the stock solution is prepared separately by successively incorporating the enzyme substrate, the solvent (S) and at least one alkyl(thio)glycoside such as defined previously, possibly adding concurrently. The products and quantities used are such as defined previously. After homogenisation, the stock solution is added to the supercooled gelled culture medium and previously regenerated in water. It may also be a non-gelled liquid medium, such as a nutrient broth, for example.

After mixing the culture medium and the stock solution, the liquid or gelled detection medium is obtained ready to be seeded.

An object of the present invention is also the use of a medium according to the invention for the detection (notably for characterisation and/or enumeration purposes) of microorganisms with esterase and/or osidase and/or peptidase and/or sulfatase and/or phosphatase activity, preferably for the detection of microorganisms with esterase activity, such as bacteria of the genus *Salmonella*.

The detection medium according to the invention may be used to:
 detect/disclose the presence or absence of microorganisms, in particular microorganisms sought (target microorganisms), and/or
 characterise said microorganisms, namely in particular to identify and/or determine their potential resistance properties to at least one anti-microbial agent (antibiotic agent in the case of bacteria), and/or
 enumerate said microorganisms.

Another object of the present invention relates to a detection medium for microorganisms with esterase and/or osidase and/or peptidase and/or sulfatase and/or phosphatase activity in a sample, preferably microorganisms with esterase activity, said method comprising the following steps:
i) seeding the medium according to the invention (as defined above) with a sample to be analysed,
ii) incubating the seeded medium in appropriate conditions (for example at 37° C. in aerobic conditions),
iii) detecting and interpreting the colorations and/or fluorescences at the colonies formed by the microorganisms, said colorations and/or fluorescences revealing the reaction of at least one chromogenic and/or fluorogenic substrate with the microbial enzyme activity which is specific to it, advantageously said enzyme activity being an esterase activity.

Said method can be employed, for example, in order to disclose the presence or absence of said microorganisms within said sample and/or in order to characterise them (for example identify them) and/or enumerate them.

The invention also relates to the use of at least one alkyl(thio)glycoside to improve the detection of an enzyme activity chosen from the esterase and/or osidase and/or peptidase and/or sulfatase and/or phosphatase activities of microorganisms, preferably said enzyme activity is an esterase activity.

The sample to be analysed may be from various origins, for example of food, environmental, veterinary or clinical origin.

Among the samples of food origin, non-exhaustive mention can be made of a sample of dairy products (yogurts, cheeses, etc.), meat, fish, egg, fruit, vegetable, water, beverages (milk, fruit juice, soda, etc.). Of course, these samples of food origin may also come from sauces or more complex meals, or from non-processed (or partially processed) raw materials. A food sample may finally come from an animal feed, such as oil cakes, animal meals.

As examples of environmental samples, mention should also be made of specimens of surface, water, air, etc.

Biological samples of clinical origin may correspond to specimens of biological fluids (whole blood, serum, plasma, urine, cerebrospinal fluid, etc.), of stools, of specimens from the nose, throat, skin, wounds, organs, tissues or isolated cells. This list is obviously not exhaustive.

Generally, the term "sample" refers to a part or a quantity (more particularly a small part or a small quantity) sampled from one or more entities for analysis purposes. This sample may possibly have undergone pretreatment, involving for example steps of mixing, diluting or even crushing, in particular if the starting entity is solid-state.

The biological sample analysed is, in general, capable of—or suspected of—containing at least one target microorganism. In the majority of cases, the latter is a pathogenic microorganism (such as *Salmonella*) which should be detected for health purposes.

The term "microorganism" has the same meaning as that generally accepted in microbiology and comprises notably Gram-positive or Gram-negative bacteria, yeasts, moulds and more generally, single-cell organisms, invisible to the naked eye, which can be manipulated and multiplied in a laboratory.

The alkyl(thio)glycoside(s) used for the purposes of the present invention is/are as defined previously. One alkyl (thio)glycoside or a plurality of alkyl(thio)glycosides (namely at least two alkyl(thio)glycosides), which preferably correspond to the general formula (I) mentioned above, are used. When at least two alkyl(thio)glycosides are used, the latter may be identical or different, all preferably corresponding to said general formula (I).

DETAILED DESCRIPTION

Example 1: Medium for Detecting Salmonellae—Improvement of the Detection Sensitivity 1.1 Preparation of the Media—Solubilisation of the Enzyme Substrates A stock solution of the enzyme substrate 5-bromo-6-chloro-3-indoxyl caprylate (magenta-C8) is made in a DMSO-type solvent. A volume of this stock solution which makes it possible to obtain a final substrate concentration of 360 mg/L is then added into flasks respectively containing Tween 20 (final concentration 6 g/L), n-octyl-β-D-glucopyranoside (OG) to final concentrations of 0.7, 2 and 6 g/L, and n-dodecyl-β-D-maltoside (DM) to the same concentrations. The different solutions are agitated and the volumes are introduced into supercooled agar media (chromID® Salmonella media). The protocol is presented in table 1 below:

TABLE 1

| Ref. Medium | T | 1 | 2 | 3 | 4 | 5 | 6 |
|---|---|---|---|---|---|---|---|
| Final substrate concentration in the medium (g/L) | 0.36 | 0.36 | 0.36 | 0.36 | 0.36 | 0.36 | 0.36 |
| Final Tween 20 concentration in the medium (g/L) | 6 | 0 | 0 | 0 | 0 | 0 | 0 |
| Final OG concentration in the medium (g/L) | 0 | 0.7 | 2 | 6 | 0 | 0 | 0 |
| Final DM concentration in the medium (g/L) | 0 | 0 | 0 | 0 | 0.7 | 2 | 6 |

The final Tween 20 concentration of 6 g/L was chosen because it is optimal in this context of solubilisation/microbiological activity.

1.2 Preparation of the Media

Microorganisms of the genus *Salmonella* from the Applicant's collection were seeded on each of the aforementioned media in accordance with the three-dial technique from bacterial suspensions calibrated to 0.5 McF. The strains were selected for their low to average expression of esterase activity, giving low to average violet coloration intensities on the chromID® *Salmonella* medium marketed by bioMérieux (under the references 43621 and 43629).

The dishes were incubated for 24 h at 37° C. Then the colonies which formed were examined visually after 24 h of incubation. The coloration intensities were recorded. The results are lodged in Table 2 below.

TABLE 2

| | T | 1 | 2 | 3 | 4 | 5 | 6 |
|---|---|---|---|---|---|---|---|
| S. enteritidis 0107018 | 2 | 1.5 | 3 | 4 | 4 | 4 | 3 |
| S. agona 0008024 | 2 | 1.5 | 3 | 4 | 4 | 4 | 3 |
| S. dublin 0008035 | 0 | 1 | 2 | 2 | 1 | 1 | 0.1 |
| S. infantis 0904097 | 2 | 1.5 | 3 | 4 | 4 | 4 | 3 |
| S. tennessee 0904084 | 1.5 | 1.5 | 3 | 4 | 4 | 3 | 2.5 |
| S. typhimurium 0011049 | 2 | 1.5 | 3 | 4 | 4 | 4 | 3 |
| S. typhimurium 0107036 | 2 | 1.5 | 2.5 | 4 | 4 | 4 | 3 |
| S. tennessee 0111019 | 2 | 2 | 3 | 4 | 4 | 3 | 2.5 |
| S. enteritidis 0107020 | 2 | 2 | 3 | 4 | 4 | 4 | 3 |
| S. infantis 0008041 | 2 | 1.5 | 2.5 | 4 | 4 | 4 | 3 |
| S. panama 0008050 | 2 | 1.5 | 3 | 4 | 4 | 4 | 3 |
| S. enteritidis 0107017 | 1.5 | 1.5 | 2.5 | 3 | 4 | 4 | 3 |
| S. panama 9009020 | 2.5 | 1.5 | 3.5 | 4 | 4 | 4 | 2.5 |

Coloration intensity: scale from 0 to 4, respectively no coloration to highly intense coloration;
0 = no coloration
0.1 = trace of coloration
0.5 = very pale coloration
1 = distinct low-intensity coloration,
2 = clear medium-intensity coloration
3 = intense coloration
4 = highly intense coloration
NB: The n.5s (for example 1.5, 2.5, 3.5) correspond to intermediate coloration intensities 1.3 Conclusion Media 2 (OG 2 g/L), 3 (OG 6 g/L), 4 (DM 0.7 g/L), 5 (DM 2 g/L) and 6 (DM 6 g/L) make it possible to obtain higher coloration intensities than the control medium T (Tween 20, 6 g/L) for all of the strains. Media 1 (OG 0.7 g/L), 2 (OG 2 g/L), 3 (OG 6 g/L), 4 (DM 0.7 g/L) and 5 (DM 2 g/L) make it possible to detect all the salmonellae tested including *S. dublin*. The media offering the best performances are media 2 (OG 2 g/L), 3 (OG 6 g/L), 4 (DM 0.7 g/L) and 5 (DM 2 g/L).

OG and DM therefore make it possible to improve the esterase activity detection sensitivity in *Salmonella*, seemingly via an improvement of this enzyme expression. Furthermore, these alkylglycosides also make it possible to detect all of the salmonellae strains tested, including *S. dublin*.

Example 2: Detection of *P. Aeruginosa* and *A. Baumannii* Via the Expression of a C9 Esterase Activity 2.1 Preparation of the Media—Solubilisation of the Enzyme Substrates Two stock solutions at 25 g/L of ALDOL™ 470-nonanoate (ALDOL 470-C9, developed by Biosynth AG, Rietlisstrasse 4,9422 Staad, Switzerland) and of ALDOL™ 495-nonanoate (ALDOL 495-C9, also developed by Biosynth AG, Rietlisstrasse 4,9422 Staad, Switzerland) are made in a DMSO-type organic solvent. Then a volume corresponding to a final concentration of enzyme substrates of 200 mg/L is added into flasks containing respectively: Tween 20 (final concentration in the medium of 6 g/L), and DM (final concentrations of 0.7, 2 and 6 g/L). The different flasks are vigorously agitated, then all of the contents are added into the supercooled agar media: TSA (trypticase soy agar) base. The composition of the different media is presented in table 3 below:

TABLE 3

| Media | 1 | 2 | 3 | 4 | 5 | 6 | 7 | 8 |
|---|---|---|---|---|---|---|---|---|
| ALDOL 470-C9 g/L | 0.2 | 0.2 | 0.2 | 0.2 | 0 | 0 | 0 | 0 |
| ALDOL 495-C9 g/L | 0 | 0 | 0 | 0 | 0.2 | 0.2 | 0.2 | 0.2 |
| Tween 20 g/L | 6 | 0 | 0 | 0 | 6 | 0 | 0 | 0 |
| DM g/L | 0 | 0.7 | 2 | 6 | 0 | 0.7 | 2 | 6 |

2.2 Biological Activity

Bacteria from the Applicant's collection were seeded on each of the aforementioned media in accordance with the three-dial technique from bacterial suspensions calibrated to 0.5 McF. The dishes were incubated for 24 h at 37° C. and the colonies formed were analysed visually. Thus, the colorations and the coloration intensities were recorded. The results are set out in table 4 below.

TABLE 4

| | 1 | 2 | 3 | 4 | 5 | 6 | 7 | 8 |
|---|---|---|---|---|---|---|---|---|
| P. aeruginosa 0001001 | 0 | 1.5 | 1.5 | 2 | 0 | 0.5 | 1.5 | 1.5 |
| P. aeruginosa 0002019 | 0.5 | 0.5 | 0.5 | 1.5 | 0 | 0 | 0 | 0.5 |
| P. aeruginosa 0110078 | 0.5 | 1 | 1.5 | 1.5 | 0.5 | 1 | 1 | 1.5 |
| A. baumannii 0509060 | 0 | 1.5 | 1.5 | 2 | 0 | 1 | 2 | 2 |
| A. baumannii 0202018 | 0 | 0.5 | 0.5 | 0.5 | 0 | 0 | 0 | 0.5 |
| A. baumannii 0409007 | 0.5 | 2 | 2 | 2 | 0 | 1.5 | 2 | 2.5 |
| A. baumannii 9811074 | 0 | 1 | 1.5 | 1.5 | 0 | 1 | 2 | 2.5 |
| A. baumannii 9809057 | 0 | 0.5 | 0.5 | 0.5 | 0 | 0.5 | 1 | 1 |

Coloration intensity: scale from 0 to 4, respectively no coloration to highly intense coloration;
0 = no coloration
0.1 = trace of coloration
0.5 = very pale coloration
1 = distinct low-intensity coloration,
2 = clear average-intensity coloration
3 = intense coloration
4 = highly intense coloration
NB: The n.5s (for example 1.5, 2.5, 3.5) correspond to intermediate coloration intensities

2.3 Conclusion

P. aeruginosa and A. baumannii are bacteria known as being esterase-positive. Control media 1 and 5 do not make it possible to reflect this characteristic. Indeed, the coloration intensities are low (0.5) or zero for the majority of the strains tested—with these 2 ALDOL™-based enzyme substrates (containing Tween 20 as a surface active agent).

The replacement of the Tween 20 at 6 g/L by DM at the same concentration unexpectedly makes it possible to improve the expression of esterase activity. Indeed, this substitution makes it possible to detect all of the strains tested, with decent coloration intensities whatever the enzyme substrate tested. A very strong impact of DM is noted on the expression of esterase activity when the substrate is ALDOL™-based.

The substitution of Tween 20 by n-dodecyl-β-D-maltoside (DM) improves the detection of the esterase activity of the microorganisms, seemingly due to better biological activity of the esterase substrates, which is manifested by a more intense coloration of the target microorganism.

The alkylglycoside according to the invention offers improved detection sensitivity and even makes it possible to detect certain colourless strains in the presence of Tween.

Furthermore, since the coloration or fluorescence intensities are higher (due to said alkylglycosides), the enzyme substrate concentration can thus be reduced, which represents an advantage in economic terms.

Example 3: Medium for Detecting Salmonellae Via the Use of an Esterase (Lipase) Substrate with 16 Carbon Atoms—Improvement of the Detection Sensitivity

3.1 Preparation of the Media—Solubilisation of the Enzyme Substrate

A stock solution of the enzyme substrate 5-bromo-4-chloro-3-indoxyl palmitate (X—C16) is made in a DMSO-type solvent. A volume of this stock solution which makes it possible to obtain a final substrate concentration of 100 mg/L is then added into flasks respectively containing Tween 20 (final concentrations of 0.1%, 0.2% and 0.6% by volume), n-octyl-β-D-glucopyranoside (OG) to final concentrations of 2 g/L, an OG (2 g/L) and Tween 20 mixture (0.1% volume), and n-octyl-β-D-thioglucopyranoside (OTG) to a final concentration in the medium of 2 g/L. The different solutions are agitated and the volumes are introduced into supercooled agar media (chromID® Salmonella media). A summary of the composition of the various media is given in table 5 below.

TABLE 5

| Medium ref. | 1 | 2 | 3 | 4 | 5 |
|---|---|---|---|---|---|
| Final concentration of X-C16 in the medium (g/L) | 0.1 | 0.1 | 0.1 | 0.1 | 0.1 |
| Final concentration of Tween 20 in the medium (% vol.) | 0.1 | 0.2 | 0 | 0.1 | 0 |
| Final concentration of OG in the medium (g/L) | 0 | 2 | 2 | 2 | 0 |
| Final concentration of OTG in the medium (g/L) | 0 | 0 | 0 | 0 | 2 |

3.2 Seeding of the Media

Microorganisms of the genus Salmonella, from the Applicant's collection were seeded on each of the aforementioned media in accordance with the three-dial technique from bacterial suspensions calibrated to 0.5 McF. The strains were chosen for their different level of expression of the esterase activity. A strain corresponding to the strain from collection ATCC 25922 of E. coli serves as negative control for the expression of such an enzyme activity.

The dishes were incubated for 24 h at 37° C. Then the colonies formed were examined visually after 24 h of incubation. The coloration intensities were recorded. The results are lodged in table 6 below.

TABLE 6

| | 1 | 2 | 3 | 4 | 5 |
|---|---|---|---|---|---|
| S. infantis 0904097 | 1 | 1.5 | 2.5 | 2.5 | 2.5 |
| S. enteritidis 0107017 | 1 | 1 | 2.5 | 2.5 | 2 |

TABLE 6-continued

| | 1 | 2 | 3 | 4 | 5 |
|---|---|---|---|---|---|
| S. typhimurium 0011049 | 1 | 1 | 2.5 | 2 | 2 |
| S. panama 0008050 | 1.5 | 1.5 | 2.5 | 2 | 2 |
| S. panama 9009020 | 1 | 1.5 | 2.5 | 2 | 2.5 |
| S. typhimurium 0107036 | 1.5 | 1.5 | 2.5 | 2.5 | 2 |
| S. enteritidis 0107020 | 1 | 1 | 2.5 | 2 | 2 |
| S. enteritidis 0107018 | 1 | 1.5 | 2.5 | 2 | 2 |
| S. tennessee 0904084 | 1 | 1.5 | 2.5 | 2 | 2 |
| S. infantis 0008041 | 1.5 | 1.5 | 2.5 | 2.5 | 2.5 |
| S. dublin 0008035 | 0 | 0 | 2 | 1.5 | 0.1 |
| S. agona 0008024 | 1 | 1 | 2.5 | 2 | 2 |
| S. dublin 0204046 | 0 | 0 | 2.5 | 1.5 | 0 |
| S. tennessee 0111019 | 1 | 1.5 | 2.5 | 2 | 2 |
| E. coli 1105059 | 0 | 0 | 0 | 0 | 0 |

Coloration intensities: scale from 0 to 4, respectively no coloration to highly intense coloration;
0 = no coloration
0.1 = trace of coloration
0.5 = very pale coloration
1 = distinct low-intensity coloration,
2 = clear medium-intensity coloration
3 = intense coloration
4 = highly intense coloration
Note:
the intensities denoted n.5 (for example 1.5 and 2.5) represent intermediate intensities.

3.3 Conclusion

Media 3, 4 and 5 make it possible to obtain higher coloration intensities than on the control medium (medium 1), comprising neither OG, nor OTG.

It is further noted that the media containing OG, alone or in mixture with Tween 20 (in particular especially when OG is used alone as in medium 3), make it possible to obtain the best performance: 100% detection sensitivity on these media with high coloration intensities for all of the strains, including S. dublin.

The E. coli strain, esterase-negative, did not appear positive, which indicates that the specificity of detection is preserved.

The invention claimed is:

1. A microorganism detection medium comprising:
    at least one chromogenic and/or fluorogenic substrate capable of being hydrolyzed by an esterase;
    at least one alkylthioglycoside or at least one alkylglycoside; and
    at least one solvent,
wherein the detection medium comprises a culture medium suitable for growing a target microorganism, wherein the at least one alkylthioglycoside or at least one alkylglycoside corresponds to the general formula (I):

$$R\text{—}X\text{-}(G)_n \qquad (I)$$

wherein:
    R represents a linear or branched, saturated or unsaturated, aliphatic radical containing 6 to 12 carbon atoms;
    X is —O— or —S—;
    G represents a carbohydrate residue; and
    n is an integer between 1 and 10.

2. The medium according to claim 1, wherein the at least one alkylglycoside is an alkylglycoside selected from the group consisting of n-octyl-β-D-glucopyranoside and n-dodecyl-β-D-maltoside.

3. The medium according to claim 1, wherein the concentration of the at least one alkylthioglycoside or at least one alkylglycoside in the medium is from 0.5 g/L to 8 g/L.

4. The medium according to claim 1, wherein the solvent is selected from the group consisting of alcohols, polar aprotic solvents, aqueous solvents, and mixtures thereof.

5. The medium according to claim 1, wherein the chromogenic and/or fluorogenic substrate comprises:
    a target part capable of being hydrolyzed by the enzyme; and
    a marker part comprising a chromophore and/or fluorophore.

6. The medium according to claim 1, wherein the chromogenic and/or fluorogenic substrate comprises indoxyl or derivatives thereof.

7. The medium according to claim 6, further comprising an agent which promotes the oxidative polymerization of the indoxyl or derivatives thereof.

8. The medium according to claim 1, wherein the concentration of chromogenic and/or fluorogenic substrate is from 1 mg/L to 10 g/L.

9. The medium according to claim 1, wherein the culture medium is selected from the group consisting of MacConkey media, Hektoen selective media, selective chromogenic media for selectively detecting *salmonella*, chromogenic *Salmonella* media, Columbia ANC media, PALCAM media, Sabouraud gentamycin-chloramphenicol type media, non-selective Columbia +/−blood media, Trypticase Soy Agar (TSA) media, nutrient agar media, and Sabouraud media.

10. The medium according to claim 1, wherein the at least one alkylglycoside is n-dodecyl-β-D-maltoside.

11. The medium according to claim 1, wherein n is an integer between 1 and 3.

12. The medium according to claim 7, wherein the agent comprises an ammonium ferric citrate complex.

13. The medium according to claim 1, wherein the at least one alkylthioglycoside is n-octyl-β-D-thioglucopyranoside.

14. The medium according to claim 1, wherein R represents a linear or branched, saturated or unsaturated, aliphatic radical containing 8 to 12 carbon atoms.

* * * * *